(12) United States Patent
Primus et al.

(10) Patent No.: US 8,308,478 B2
(45) Date of Patent: Nov. 13, 2012

(54) METHODS FOR INDIRECT BONDING OF ORTHODONTIC APPLIANCES

(75) Inventors: Carolyn M. Primus, Bradenton, FL (US); Michael C. Alpern, Port Charlotte, FL (US); Michael Anderson, Palmetto, FL (US)

(73) Assignee: DENTSPLY International Inc., York, PA (US)

( * ) Notice: Subject to any disclaimer, the term of this patent is extended or adjusted under 35 U.S.C. 154(b) by 259 days.

(21) Appl. No.: 12/291,363

(22) Filed: Nov. 7, 2008

(65) Prior Publication Data

US 2009/0220920 A1 Sep. 3, 2009

Related U.S. Application Data

(63) Continuation-in-part of application No. 11/649,666, filed on Jan. 4, 2007, now abandoned, which is a continuation-in-part of application No. 11/214,152, filed on Aug. 29, 2005, now abandoned, which is a continuation-in-part of application No. 11/069,303, filed on Mar. 1, 2005, now abandoned.

(51) Int. Cl.
*A61C 3/00* (2006.01)

(52) U.S. Cl. .............................. 433/24; 433/9
(58) Field of Classification Search .......... 433/8, 9, 433/10, 39, 2, 3, 24
See application file for complete search history.

(56) References Cited

U.S. PATENT DOCUMENTS

| | | |
|---|---|---|
| 3,738,005 A | 6/1973 | Cohen et al. |
| 3,949,477 A | 4/1976 | Cohen et al. |
| 4,204,325 A | 5/1980 | Kaelble |
| 5,015,180 A | 5/1991 | Randklev |
| 5,098,288 A | 3/1992 | Kesling |
| 5,147,202 A | 9/1992 | Masuhara et al. |
| 5,195,824 A | 3/1993 | Stromberg et al. |
| 5,219,283 A | 6/1993 | Farzin-Nia et al. |
| 5,263,859 A | 11/1993 | Kesling |
| 5,267,855 A | 12/1993 | Tuneberg |
| 5,295,284 A | 3/1994 | Demuth et al. |

(Continued)

FOREIGN PATENT DOCUMENTS

EP 1620031 B1 9/2008

(Continued)

OTHER PUBLICATIONS

Elliott M. Moskowitz et al—A New Look at Indirect Bonding—Journal of Clinical Orthodontics; vol. 30, No. 5, pp. 277-281, 1996.

(Continued)

*Primary Examiner* — Cris L Rodriguez
*Assistant Examiner* — Eric Rosen
(74) *Attorney, Agent, or Firm* — David A. Zdurne; Douglas J. Hura; Leana Levin (57) ABSTRACT

Improved methods for indirect bonding of orthodontic appliances, such as brackets, to the tooth surfaces of dental patients are provided. The methods use a transfer tray to accurately position the brackets on the tooth surfaces. Preferably, the tray is made of an ethylene vinyl acetate copolymer (EVA)/siloxane material. The brackets are coated with a protective coating to prevent them from becoming embedded in the tray. Preferably, a translucent, blue-tinted coating is used to cover the brackets. Dental restorative materials are used to bond the brackets to the teeth. The transfer tray is then removed from the mouth, while the appliances remain firmly bonded to the tooth surfaces.

29 Claims, 6 Drawing Sheets

U.S. PATENT DOCUMENTS

| | | | |
|---|---|---|---|
| 5,328,363 A | 7/1994 | Chester et al. | |
| 5,480,301 A | 1/1996 | Farzin-Nia et al. | |
| 5,558,516 A | 9/1996 | Horn et al. | |
| 5,575,645 A * | 11/1996 | Jacobs et al. | 433/9 |
| 5,810,584 A | 9/1998 | Wong | |
| 5,890,892 A | 4/1999 | Lemchen | |
| 5,897,312 A | 4/1999 | Chikami | |
| 5,971,754 A | 10/1999 | Sondhi et al. | |
| 6,050,815 A | 4/2000 | Adam et al. | |
| 6,060,815 A | 5/2000 | Nysen | |
| 6,120,288 A | 9/2000 | Deslawiers | |
| 6,183,249 B1 | 2/2001 | Brennan et al. | |
| 6,238,212 B1 | 5/2001 | Khachatoorian et al. | |
| 6,350,120 B1 | 2/2002 | Sachdeva et al. | |
| 6,364,659 B1 | 4/2002 | Lotte | |
| 6,384,099 B1 | 5/2002 | Ostler et al. | |
| 6,398,548 B1 | 6/2002 | Mukhammad et al. | |
| 6,435,870 B1 | 8/2002 | Walde | |
| 6,464,496 B1 | 10/2002 | Sachdeva et al. | |
| 6,471,512 B1 | 10/2002 | Sachdeva et al. | |
| 6,482,002 B2 | 11/2002 | Jordan et al. | |
| 6,528,555 B1 | 3/2003 | Nikutowski et al. | |
| 6,540,512 B1 | 4/2003 | Sachdeva et al. | |
| 6,554,611 B2 | 4/2003 | Chishti et al. | |
| 6,554,613 B1 | 4/2003 | Sachdeva et al. | |
| 6,565,355 B2 | 5/2003 | Kim et al. | |
| 6,621,491 B1 | 9/2003 | Baumrind et al. | |
| 6,632,089 B2 | 10/2003 | Rubbert et al. | |
| 6,644,968 B2 | 11/2003 | Orikasa et al. | |
| 6,648,640 B2 | 11/2003 | Rubbert et al. | |
| 6,685,468 B1 | 2/2004 | Kesling | |
| 6,688,885 B1 | 2/2004 | Sachdeva et al. | |
| 6,722,880 B2 | 4/2004 | Chishti et al. | |
| 6,746,242 B1 | 6/2004 | Kesling | |
| 6,749,426 B2 | 6/2004 | Devanathan | |
| 6,776,614 B2 | 8/2004 | Wiechmann et al. | |
| 6,830,450 B2 | 12/2004 | Knopp et al. | |
| 6,905,337 B1 | 6/2005 | Sachdeva | |
| 6,918,761 B2 | 7/2005 | Sachdeva et al. | |
| 6,928,733 B2 | 8/2005 | Rubbert et al. | |
| 6,947,038 B1 | 9/2005 | Anh et al. | |
| 6,960,079 B2 | 11/2005 | Brennan et al. | |
| 6,971,873 B2 | 12/2005 | Sachdeva et al. | |
| 7,013,191 B2 | 3/2006 | Rubbert et al. | |
| 7,020,963 B2 | 4/2006 | Cleary et al. | |
| 7,029,275 B2 | 4/2006 | Rubbert et al. | |
| 7,033,327 B2 | 4/2006 | Raby | |
| 7,056,115 B2 | 6/2006 | Phon et al. | |
| 7,131,836 B1 | 11/2006 | Kesling | |
| 7,133,042 B2 | 11/2006 | Anh et al. | |
| 7,134,874 B2 | 11/2006 | Chishti et al. | |
| 7,137,812 B2 | 11/2006 | Cleary et al. | |
| 7,155,373 B2 | 12/2006 | Jordan et al. | |
| 7,160,110 B2 | 1/2007 | Imgrund et al. | |
| 7,172,417 B2 | 2/2007 | Sporbert et al. | |
| 7,186,114 B2 | 3/2007 | Navarro et al. | |
| 7,188,421 B2 | 3/2007 | Cleary et al. | |
| 7,217,124 B2 | 5/2007 | Cinader, Jr. et al. | |
| 7,252,509 B2 | 8/2007 | Sachdeva | |
| 7,291,011 B2 | 11/2007 | Stark et al. | |
| 7,293,988 B2 | 11/2007 | Wen | |
| 7,335,024 B2 | 2/2008 | Wen | |
| 7,336,763 B2 | 2/2008 | Spartiotis et al. | |
| 7,347,688 B2 | 3/2008 | Kopelman et al. | |
| 7,347,690 B2 | 3/2008 | Jordan et al. | |
| 7,354,268 B2 | 4/2008 | Raby et al. | |
| 7,361,017 B2 | 4/2008 | Sachdeva et al. | |
| 7,374,420 B2 | 5/2008 | Brennan et al. | |
| 7,383,198 B1 | 6/2008 | Sepe | |
| 7,384,266 B2 | 6/2008 | Wen | |
| 7,387,511 B2 | 6/2008 | Marshall | |
| 7,404,714 B2 | 7/2008 | Cleary et al. | |
| 7,410,357 B2 | 8/2008 | Cleary et al. | |
| 2003/0198913 A1 | 10/2003 | Cinader, Jr. et al. | |
| 2003/0207224 A1 * | 11/2003 | Lotte | 433/6 |
| 2004/0121279 A1 | 6/2004 | Kelly | |
| 2004/0219471 A1 * | 11/2004 | Cleary et al. | 433/3 |
| 2005/0065568 A1 | 3/2005 | Liu et al. | |
| 2005/0074716 A1 | 4/2005 | Cleary et al. | |
| 2005/0136370 A1 | 6/2005 | Brennan et al. | |
| 2006/0099544 A1 | 5/2006 | Lai et al. | |
| 2006/0099545 A1 | 5/2006 | Lai et al. | |
| 2006/0160043 A1 | 7/2006 | Cleary et al. | |
| 2006/0166160 A1 | 7/2006 | Cleary et al. | |
| 2006/0177791 A1 | 8/2006 | Cinader, Jr. et al. | |
| 2006/0183080 A1 * | 8/2006 | Nosov et al. | 433/215 |
| 2006/0223031 A1 | 10/2006 | Cinader et al. | |
| 2007/0111152 A1 | 5/2007 | Primus et al. | |
| 2007/0287121 A1 | 12/2007 | Cinader et al. | |
| 2008/0138771 A1 * | 6/2008 | Knutson | 433/223 |
| 2008/0187878 A1 | 8/2008 | Brennan et al. | |
| 2008/0233528 A1 * | 9/2008 | Kim et al. | 433/2 |
| 2008/0233530 A1 | 9/2008 | Cinader | |
| 2008/0233531 A1 | 9/2008 | Raby et al. | |
| 2008/0293004 A1 | 11/2008 | Lemcken | |
| 2009/0239190 A1 * | 9/2009 | Darnell | 433/48 |

FOREIGN PATENT DOCUMENTS

| | | |
|---|---|---|
| EP | 1562511 B1 | 4/2010 |
| WO | 2004024885 A2 | 3/2004 |
| WO | 2004039883 A1 | 5/2004 |
| WO | 2004041116 A2 | 5/2004 |
| WO | 2004041704 A1 | 5/2004 |

OTHER PUBLICATIONS

Uysal et al, Angle Orthodontics vol. 74, No. 5, p. 694, 2004.

* cited by examiner

METHODS FOR INDIRECT BONDING OF ORTHODONTIC APPLIANCES

CROSS-REFERENCE TO RELATED APPLICATIONS

This application is a continuation-in-part of application Ser. No. 11/649,666 filed on Jan. 4, 2007, now abandoned which is a continuation-in-part of application Ser. No. 11/214,152 filed Aug. 29, 2005, now abandoned which is a continuation-in-part of application Ser. No. 11/069,303 filed Mar. 1, 2005, now abandoned the entire contents of which are hereby incorporated by reference.

BACKGROUND OF THE INVENTION

1. Field of the Invention

The present invention relates generally to improved methods for indirect bonding of orthodontic appliances, such as brackets, to the tooth surfaces of dental patients. The methods use a transfer tray to accurately position the brackets on the tooth surfaces. Dental materials are used to bond the brackets to the teeth. The tray is then removed from the mouth, while the appliances remain firmly bonded to the tooth surfaces. One advantage of the tray system is the tray material securely holds the brackets and blocks out all bracket undercuts.

2. Brief Description of the Related Art

Orthodontic treatment is performed to move poorly positioned teeth to new locations, which leads to improved occlusion of opposing teeth in the oral cavity. The motivation for orthodontic treatment can be improved appearance, correction of congenital defects, reduction of temporal-mandibular joint pain, enhanced masticatory function, alleviation of trauma-induced mal-positioning of teeth, correction of age-related tooth movement due to loss of other teeth or the eruption of third molars, or reduction of periodontal trauma caused by malocclusion.

Orthodontic appliances (bands, brackets, anchorage devices, and occlusal separators) are commonly bonded to each tooth individually, and a wire in the lower and upper dental arch connects the appliances. The placement of these appliances on each tooth is of the utmost important to the treatment for each tooth's position with regard to moving the teeth to the desired orthodontic position. If the appliance is applied too closely or too distantly from the gingival tissue, the tooth may move to a position that is unduly intruded or extruded. Similarly, if improperly placed, the desired rotation or torque may not be applied to the tooth to ensure its correct alignment in the dental arch.

In general, there are two techniques for bonding the orthodontic appliances to the tooth surfaces of the patient: i) direct bonding and ii) indirect bonding. In a direct bonding method, the appliance is placed directly on the tooth surface. The base of the appliance and/or tooth surface must be coated with adhesive. Once the appliance is properly positioned, the adhesive is cured to bond the appliance in place. Light-curing, and chemical (self)-curing, and dual-curing adhesives may be employed. While the direct bonding technique is commonly used, it can have some disadvantages. For instance, it can be difficult for the practitioner to accurately place the appliance in its intended location. The appliance may shift slightly as it is being bonded on the tooth surface. The process can be time-consuming as each appliance must be precisely positioned and then bonded in place with limited time and limited vision into the oral cavity.

In an indirect bonding method, a dental laboratory or clinician makes a transfer tray having the shape of a patient's dental anatomy. A set of appliances is releasably attached to the transfer tray. When the patient is ready, the base of the appliance and/or tooth surfaces must be coated with adhesive. The transfer tray is then placed in the patient's mouth and pressed over the patient's teeth until the adhesive cures. The tray is then removed from the mouth, while the appliances remain firmly bonded to the tooth surfaces. Thus, the appliances are transferred from the tray and become bonded to the tooth surfaces at their desired locations. Some indirect bonding techniques are generally described in the literature. Early techniques as described in Cohen and Silverman, U.S. Pat. No. 3,738,005, required engagement of the tray into the hooks and undercuts of the brackets for transfer.

Recent methods, as described in Cleary et al., U.S. Pat. Nos. 7,020,963, 7,404,714, 7,410,357, and 7,188,421 use an indirect bonding tray that is made by initially placing spacer material, such as silicone, over a replica of the patient's tooth structure. A tray is then formed over the spacer material and hardened. Once the tray has hardened, the tray is detached from the spacer material. Next, the spacer material is removed from the tooth replica and set aside. The orthodontic appliances are placed on the replica at the desired locations. A silicone matrix or dental impression material is placed between the tray and replica and allowed to harden. Then, the tray assembly can be removed from the replica for insertion in the patient's mouth and the brackets can be transferred and bonded to the patient's teeth.

Although some indirect bonding techniques are generally effective for bonding orthodontic appliances, there is a need for improved methods. The present invention provides such improved methods.

SUMMARY OF THE INVENTION

The present invention relates to improved methods for bonding orthodontic appliances such as, brackets to tooth surfaces. In the first phase of the method, which can be performed by a dental laboratory, an indirect bonding transfer tray is made. This generally involves the steps of: i) providing an orthodontic bracket having a main body with a tooth-engaging surface, wherein the surface is coated with at least one dental restorative material, ii) making a dental model of a patient's dental anatomy; iii) positioning the brackets on the tooth surfaces of the model; iv) applying a polymeric material to cover at least a portion of each bracket; v) forming a tray over the model so that the tray conforms to the model's shape and the brackets become releasably attached to the tray; and vi) removing the tray with the attached brackets from the model. In the next phase, the tray is inserted into the patient's mouth at the dental office and this generally involves the steps of: vii) preparing the patient's tooth surfaces to be fitted with the brackets; viii) applying at least one dental restorative, which functions as an adhesive, to the appliances in the tray, and pressing the tray into position in the patient's mouth so the brackets are properly aligned and bonded to the tooth surfaces; and ix) removing the tray from the patient's mouth so the brackets remain bonded to the tooth surfaces.

In one preferred embodiment, a translucent, blue-tinted coating is used to cover the body of the bracket. The blue coating can comprise a variety of materials such as, for example, silicone, polyvinylsiloxane or polyether materials. This blue coating forms a protective covering and provides high visibility. Thus, the dental clinician is better able to see and remove the material from the patient's mouth during the finishing step. Furthermore, the blue color does not block blue light radiation during the intraoral curing steps. Preferably, the tray material is made of a blend of ethylene vinyl acetate copolymer (EVA) and siloxane. This tray material has several advantageous properties as discussed further below including high strength and elasticity so that it is highly durable and can conform tightly to the shape of the dental model. Most importantly, the EVA/siloxane tray material does not warp or (creep) after forming and it does not distort after being removed from the dental model.

DETAILED DESCRIPTION OF THE INVENTION

The present invention provides improved methods for indirect bonding of orthodontic appliances. Although the methods are described primarily herein as being used to place orthodontic brackets, it should be understood this is for illustration purposes only and the methods are not restricted to placing brackets. The methods can be used to place any orthodontic appliance such as tubes, lingual attachment buttons, lingual brackets, and inter-arch spacers. Furthermore, this method can be used to bond such devices to the occlusal buccal/labial or lingual portions of tooth, separately or in combination. The methods can also be used to make specialized retainers or tooth positioners for minor tooth movement or bonded lingual retainers.

A patient undergoing orthodontic treatment will typically make several office visits to dental professionals. For example, the patient may need appointments with general dental practitioners, pediatric dentists, orthodontists, and others. These dental professionals are collectively referred to herein as dental clinicians. In one visit, the clinician takes an initial impression of the patient's dental anatomy. Alginate impressions are made commonly. For higher accuracy and more durable impressions, polyether or polyvinyl siloxane impression material is used. The higher quality impression materials are normally prepared from two paste components, for instance, elastomeric material such as vinyl-terminated polysiloxanes capable of undergoing polymerization. Once the pastes are mixed together, they start to harden and form a rubbery material. Bite trays for the upper and lower dental arches (teeth) can be prepared by dispensing the impression material into a bite tray. The tray is inserted in the patient's mouth, surrounding either the upper or lower teeth, and the impression material is allowed to cure and harden. Then, the tray is removed from the mouth. To make a negative impression of the upper teeth, the tray is inserted over the upper dental arch. In a similar manner, a bite tray for taking an impression of the lower dental arch can be prepared. It should be understood that alternative methods can be used to take the impression of the patient's dental anatomy. For example, in recent years, new digital imaging techniques for taking dental impressions have been developed, and these techniques can be used in accordance with this invention.

I. Fabrication of Indirect Bonding Transfer Tray at Dental Laboratory.

Normally, the hardened impressions are sent to an outside dental laboratory that will fabricate the transfer tray, although the techniques may be performed in the dental office if so equipped. The dental technician at the laboratory or the clinician prepares a cast (model) by pouring dental plaster (stone) into the hardened impression. It is recognized that other methods and materials (such as epoxies) can be used to make the dental model. For example, digital imaging techniques can be used. The models are trimmed and finished. The finished model has shaped surfaces closely matching the patient's upper and lower dental arches.

Figure 2:
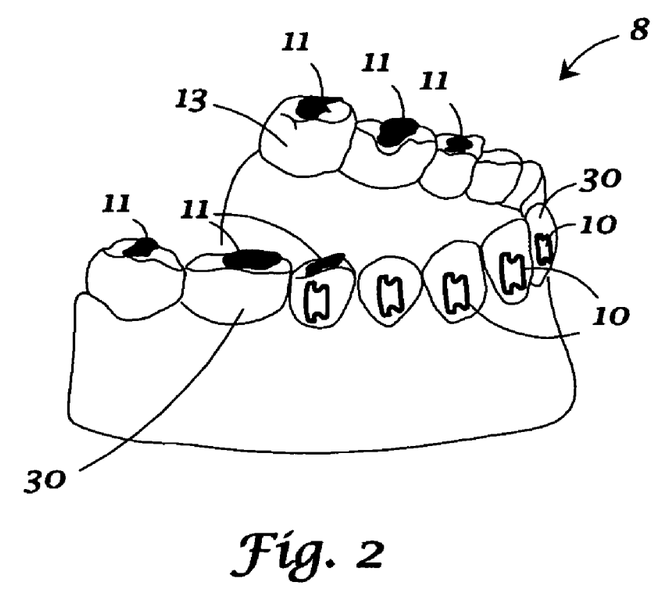
FIG. 2 is perspective view of a dental model showing orthodontic devices bonded to tooth surfaces (buccal/labial and lingual) and having areas where an occlusal separation material is applied to the teeth, in accordance with this invention.
Figure 3:
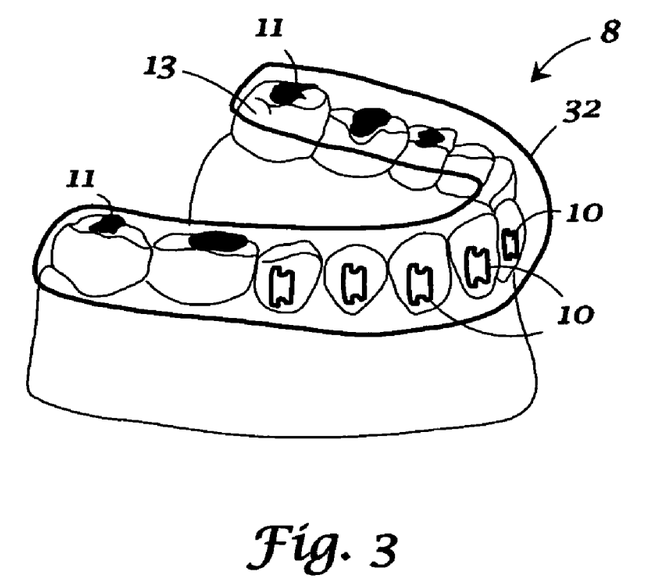
FIG. 3 is a perspective view of a transfer tray positioned over the dental model of FIG. 2 after protective coatings have been applied to the brackets in accordance with this invention.

In FIGS. 2 and 3, a dental model (8) is shown. Orthodontic brackets (10), a lingual attachment button (13), and occlusal inter-arch separator material (11) have been applied to the replica tooth surfaces (30) of the dental model (8) using techniques described further below. It should be understood that FIGS. 2 and 3 show the joint application of the brackets (10), lingual button (13), and separator material (11) to the model (8) for illustrative purposes, and it is not necessary for these devices/materials to be applied together. The description herein primarily refers to the brackets (10).

In practice, preferably, a separating liquid is applied to the dental model (8) prior to positioning the orthodontic brackets (10) on the model. The separating liquid helps make removing the brackets (10) and separator materials (11) and lingual buttons (13) from the model (8) at a later point easier. When the separating liquid is applied, the brackets (10) and other materials/devices (11, 13) still maintain good bonding to the model (8) during construction of the transfer tray. When it comes time to remove the transfer tray (32) from the model (8), the separating liquid helps facilitate this removal and prevents the materials/devices (10, 11, 13) from incorporating any dental stone or other material of which the replica (8) is made. The transfer tray (32) and its component devices (10, 11, 13) can be detached easily from the model (8) using this technique. Very little, if any, debris is removed from the model (8) when the tray (32) is pulled off. The separating liquid may contain mineral oils, vegetable oil, silica sols, silica gel, polyvinyl alcohol solutions, polyvinylpyrrolidone solutions, methyl ethyl ketone, acetone, butyl acetate, and alcohols including glycerol, isopropanol, ethanol, methanol, or sorbitol. Combinations of the foregoing ingredients may also be used. Preferably, the separating liquid is soluble or miscible in water.

Figure 1:
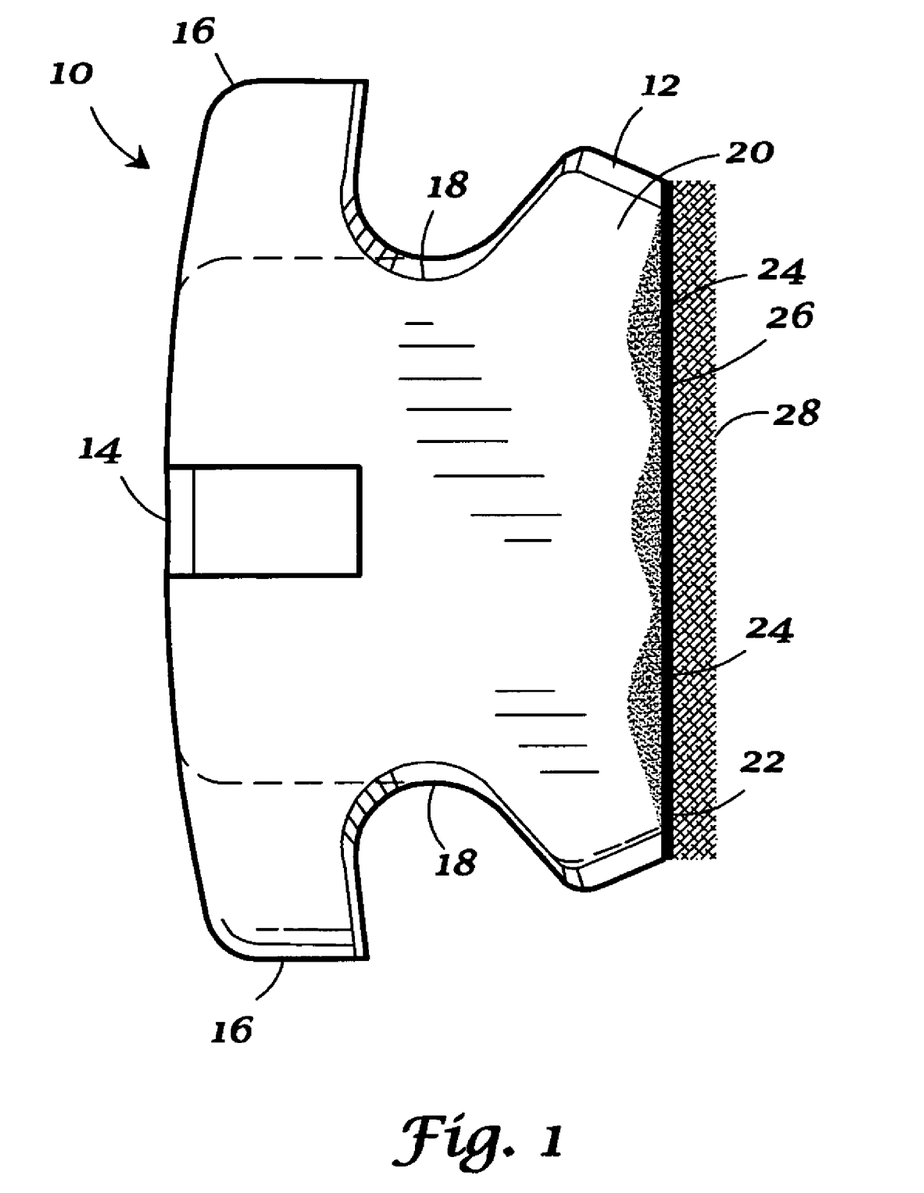
FIG. 1 is a side perspective view of a ceramic orthodontic bracket having a bracket base coated with two layers of curable dental restorative materials that can be bonded to a dental model in accordance with this invention.

In the next step, the brackets (10), lingual attachment devices (13), and occlusal separator material (11) are positioned on the targeted tooth surfaces (30) of the dental model (8) and bonded thereto. In the present invention, the tooth-engaging surface (22) of the base (20) of the bracket (10) or lingual attachment devices (13) are preferably pre-cemented with first and second dental restorative materials (26, 28) before being applied to the model (FIG. 1).

The base (20) of the bracket (10) normally is covered with a layer of mesh material or it has a rough surface (22) with minute undercuts (24) to improve the bonding effect. The mesh material or rough surface (22) helps to improve bonding strength between the bracket (10), dental materials (26, 28), and tooth. More particularly, for metal brackets, the base plate is usually covered with a mesh material. The mesh material can have openings of various sizes. For example, 80-mesh size material has openings of about 180 μm; 170-mesh size material has openings of about 75 μm; and 400-mesh size material has openings of about 38 μm. For ceramic brackets (10), the base plate (20) has a rough surface (22) with undercuts (24), which can range from microscopic etched irregularities to macroscopic channels. A first dental restorative material (26) is applied to the mesh material or roughened surface (22) of the bracket base (20) in accordance with this invention.

It has been found that one problem with using brackets (10) is that there is a relatively high undercut or open area on the tooth-engaging surface (22) of the base (20) of the bracket (20). Applying an ordinary orthodontic adhesive to the mesh material can be difficult, because commonly used orthodontic adhesive materials tend to remain on the outer surface of the base (20) and do not penetrate and surround each microscopic or macroscopic protuberance (24) completely. If the bracket base (20) is covered with a mesh material or has a relatively large undercut area, that is, a very fine mesh or vast number of closely spaced undercuts, it is has been found that a preferred way of coating the surface (22) of the base (20) is to use a dental restorative material having a relatively low viscosity. Preferably, this first dental restorative material (26) has a viscosity in the range of 1.4 to 1000 Pascal-seconds (Pa·s). Among dental restorative materials, there are one-component and multi-component chemically curable or light-curable composite resins, glass ionomers, and compomers that can be used in accordance with this invention. These materials penetrate and surround the undercuts on the tooth-engaging surface (22) of the orthodontic appliance (10). Preferably, the first dental restorative material (26) is cured prior to the next step.

After the coated layer of first dental material (26) has been cured, a second dental restorative material (28), having a relatively high viscosity can be coated over the first dental material layer (26). Preferably, the second dental restorative material (28) has a viscosity in the range of 2000 to 5000 (Pa·s). Suitable second dental restorative materials (28) include, for example, chemically-cured, dual-cured or light-curable dental materials based on methacrylates. Preferably, this second dental restorative material (28) is not cured prior to positioning the bracket (10) or lingual attachment (13) on the model (8).

The orthodontic brackets (10) and lingual buttons (13) so coated are positioned precisely on the model (8). Before curing, the model (8) can be moved to various angles to ensure the devices are precisely positioned in the best location to effect orthodontic movement and alignment. This ability to view the model (8) from the occlusal, gingival, posterior, and other angles is not possible with conventional direct bonding methods and is a benefit of the indirect method of this invention. After the precise position is reached, the material (28) is cured.

In a preferred version of this invention, dental restorative materials are used as the first and second dental materials (26, 28) in attaching the brackets (10) to the tooth surfaces (30). These materials are known in the art and contain photopolymerizable resins such as acrylate or methacrylate resins (for example, ethoxylated bisphenol A dimethacrylate (EBPADMA); urethane dimethacrylate (UDMA) and triethylene glycol dimethacrylate (TEGDMA)); polymerization initiators (for example, camphorquinone (CQ)); polymerization accelerators (for example, ethyl 4-dimethylamino benzoate (EDMAB)); filler particles (for example, silica and glasses); and additives (for example, blue or ultraviolet-light absorbers, anti-oxidants, plasticizers, and the like). Alternatively glass-ionomer materials (based on the reaction of silicate glass powder that is usually a fluoroaluminosilicate, and polyalkeonic acid) may be used alone or in combination with such photopolymerizable resins.

The restorative materials (26, 28) can be light-curable, self (chemically)-curable, or dual-curable. The materials (26, 28) cure and harden by a chemical mechanism to form a strong and durable product. Restorative materials (26, 28) are normally used by dental clinicians to make products that replace or restore lost tooth structure, teeth, or oral tissue such as fillings, inlays, onlays, veneers, crowns, and bridges. However, it has been surprisingly found that such dental restorative materials (26, 28) can be used to coat the tooth-engaging surface of the base (20) of the bracket (10) prior to bonding the bracket to the dental model (8) per this invention.

Figure 1A:
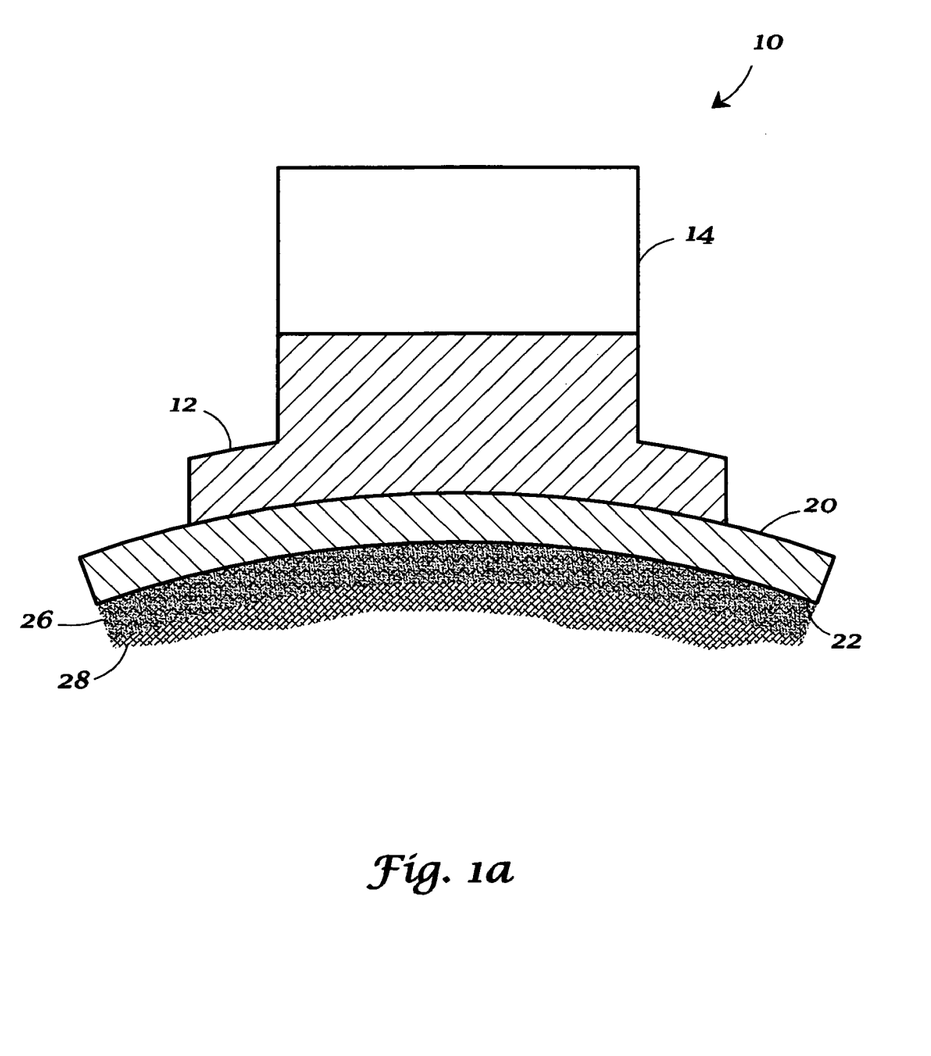
FIG. 1A is a side perspective view of a metal orthodontic bracket having a bracket base coated with two layers of curable dental restorative materials that can be bonded to a dental model in accordance with this invention.

Referring to FIGS. 1 and 1A, an orthodontic bracket, which is coated with first and second dental restorative materials (26, 28), is generally indicated at (10) and (10'), respectively. In FIG. 1, a ceramic bracket (10) is shown and in FIG. 1A, a metal bracket is shown. The ceramic bracket (10) is primarily referred to in the following description, but it should be understood that a metal bracket (10') and brackets made of other materials such as polycarbonate (not shown) also can be used in accordance with this invention. The bracket (10) includes a includes a main body (12) having a central longitudinal groove (14) for receiving an arch wire (not shown) used typically in dental braces and further includes upper and lower tie wings (16) defining wire tie-down grooves (18). A bracket base (20) is integrated with the main body (12) and has a tooth-engaging surface (22) with retentive elements (24). The retentive elements (24) may be formed by etching, microscopic roughening, undercuts, pockets, machining, molded into the bracket, and other indentation techniques. As described above, the first curable material (26) is applied and flows into the array of retentive elements (24). The material (26) is then cured. Thus, both mechanical and chemical bonding of the first layer (26) can occur. A second curable material (28) is then applied over the first cured material (26) as described above.

Alternatively, a single low-viscosity or intermediate-viscosity dental material can be applied to the tooth-engaging surface (22) of the bracket (10). Enough material can be used so that the base surface (22) is completely coated. That is, the single dental material completely coats the undercuts and roughened surface (22) of the base (20). Then, the bracket (10) is positioned on the model (8) and held in place until the low or intermediate-viscosity dental material is cured. The dental materials can be manually applied to the base surface (22) of the bracket (10), or the materials can be applied using any kind of injection or extrusion machine.

Preferably, the first and second dental restorative materials (26, 28) are light curable. The light-curable dental restorative materials contain a photopolymerization system capable of being activated by blue, visible light having a wavelength in the range of about 400 to 550 nm. The photoinitiator in the composition absorbs the irradiated light and generates free radicals for polymerization. Standard dental curing lights can be used to light-cure the composition. For example, Light- Emitting Diode (LED) dental curing lights such as SmartLite iQ2™ and SmartLite PS™ (Dentsply) can be used. LED curing lights normally emit light in the wavelength spectrum of about 450 to 480 nm. Alternatively, a halogen curing light, which has a broader spectral light output (390 to 500 nm), can be used. In other instances, a plasma arc curing light such as PowerPAC™ [American Dental Technologies, Corpus Christi, Tex.] and the Rembrandt Sapphire™ [Den-Mat, Santa Maria, Calif.], may be used. Plasma-arc (PAC) lights generate a high-voltage pulse that creates hot plasma between two electrodes in a xenon-filled bulb. The irradiance (up to 2400 mW/cm$^2$) is much higher than a typical halogen light, but and the PAC lights generate very high heat with a broad emission spectrum similar to halogen curing lights. Filters limit the emission spectrum to the blue spectrum. The plasma arc lights are an advantageous alternative to conventional light curing, because they significantly reduce the curing time of the dental materials (26, 28) on the orthodontic brackets (10) without affecting the bond failure rate.

In other instances, a Triad™ curing oven (Dentsply) or similar laboratory-based devices can be used to cure the dental restorative materials (26, 28). The Triad™ curing oven uses a quartz halogen bulb to initiate light curing of the material. In addition, the warmth of the illuminant in the confined chamber contributes to the curing effect.

Application of the first and second dental restorative materials (26, 28) to the brackets (10) creates a custom base surface (22). The custom base surface (22) is created by the shape of the coatings (26, 28) which fits to the irregularities of the tooth surface (37). A custom base surface (22) on each bracket (10) or lingual attachment (13) specifically and accurately accommodates the various small anatomical irregularities of the surface of the teeth (37). The result is a more precise fit, easier bracket placement, and the potential for moving the teeth more quickly and easily to the desired locations for optimum occlusion.

It is also recognized that the dental restorative materials (26, 28) can be cured using techniques other than blue-light curing; chemical, or dual-curing dental materials may be used. For example, curing of the coated dental materials (26, 28) may take place under ambient conditions or accelerated using special illumination such as blue lighting or sun exposure. Ultraviolet (UV) light-curable dental materials also can be used, as there is no danger posed to a patient by UV curing the dental material onto the base surface (22).

Commercially available products that can be used for the dental restorative materials (26, 28) in accordance with this invention include Dyract Flow™, Dyract™, Esthet X™ and Esthet X Flow™, TPH™ and TPH3™ dental materials available from Dentsply. In addition, Accolade™, Aria™, Starfill 2B™ materials available from Danville Engineering; Virtuoso™ materials from Den-Mat, Revolution™; Prodigy™ materials available from Kerr Corp; and Filtek Flowable™ or Z100™ materials available from 3M Company are suitable.

The pre-pasted brackets sold by 3M Company, such as APC™ II Adhesive Coated Appliance System or APC™ PLUS Adhesive Coated Appliance System, are also suitable for use in the indirect bonding method of this invention. If APC™ pre-pasted brackets are used in the method, the brackets must be positioned on the model while protecting the brackets from blue light that will activate curing of the adhesive. Performing the tray manufacture in a room with only yellow lamps would achieve this goal. Alternatively, the adhesives of the APC brackets can be cured in position on the model, creating a custom base on the model. In the former case, no adhesive would need to be added when the tray is placed intra-orally; in the latter case, an adhesive would be needed before intraoral placement.

Referring to FIG. 2, after the brackets (10) have been precisely positioned on the selected tooth surfaces (30) of the model (8), the dental materials (26, 28) coated on the bracket bases (not shown) are light-cured to bond the brackets (10) in place. The bond strength between the bracket (10) and tooth surface (30) is sufficiently strong so the transfer tray (32) can be constructed over the model (8) as described further below. However, the bond strength is not excessively high to prevent the bracket (10) (as attached to the transfer tray (32)) from being removed later from the model (8). Alternatively, a temporary cement material can be used to position and temporarily bond the brackets (10) to the model (8), but such materials are less preferred. If a temporary cement material is used, it must be removed and replaced with a dental adhesive material before intraoral placement of the transfer tray (32). When a temporary cement material is used, more material must be cured when the tray (32) is seated in the mouth. Also, no custom base surface (22) is created when using the temporary cement method. A custom bracket base accommodates small tooth surface irregularities or changes in anatomy, which ensure more precise and exact bracket placement and is preferred.

As further shown in FIG. 2, occlusal build-up material (11) also may be placed on the model (8) where desired to disclude the teeth. This material (11) may be a conventional dental material that will facilitate separation and movement of the teeth to their new positions. This occlusal material (11) must wear preferentially to the opposing natural teeth and should be cured prior to forming the transfer tray (32). This ensures that the occlusal build-up material (11) can be easily separated from the model (8) and later from the transfer tray (32).

Figure 4:
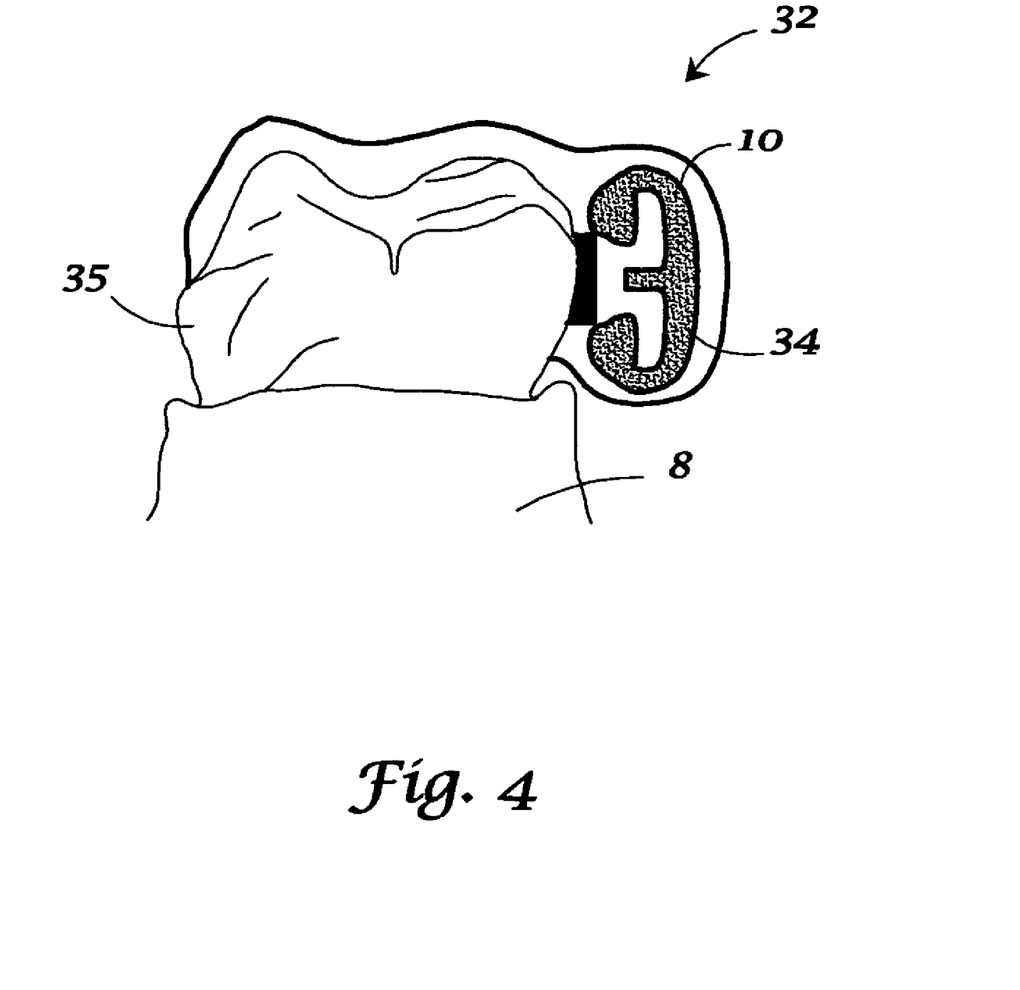
FIG. 4 is a close-up view showing a transfer tray positioned over the tooth of a dental model, wherein a bracket with a protective coating has been releasably attached to the tray in accordance with this invention.

Next, the outer body (12) (structure adjacent to the tooth-facing surface (22)) of each bracket (10) is at least partially covered with a coating of polymeric material. In FIGS. 3 and 4, the brackets (10) are shown coated with the protective covering (34). The polymeric material used for the protective coating (34) is preferably a translucent polymer, and may be a polyvinyl siloxane of a medium viscosity such as one used for crown and bridge impressions. Alternatively, a silicone paste can be used. This covering material (34) blocks out the undercuts (18) of the orthodontic brackets (10) including hooks for elastics to be attached and yet, this material (34) retains elasticity so that it can be removed later from the brackets (10). The material (34) does not warp once it cures. A colored protective material, as opposed to a translucent or clear material (34), may be used particularly over metal brackets (10').

As described in further detail below, when a translucent, blue covering material (34) is used, it can assist the orthodontist, because he/she is better able to see the material (34) and remove it from the brackets (10). This is especially helpful when ceramic brackets (10) are used. Furthermore, the blue color does not block penetration of light radiation from dental curing light beams. Coating the non-tooth-facing portion (12) of the bracket (10) is an important step in the method as the coating prevents the bracket from becoming embedded in the transfer tray (32) that will be formed subsequently over the model (8).

As illustrated in FIG. 4, the coating (34) encapsulates and forms a protective "hat" or cover over the outer portion (12, 16, 18) of the orthodontic bracket (10), which is shown bonded to a molar tooth (35) on the model (8). The hat prevents the bracket (10) from interlocking with the transfer tray (32). Furthermore, the hat helps grip the transfer tray material (32) as the material is being thermoformed over the brackets (10). Unlike other indirect bonding systems, this protective hat (34) does not extend past the outer portion (12) of the bracket (10) and does not contact the tooth surfaces (30). Extension of the protective hat (34) to the occlusal or incisal edge of the tooth is not desired in contrast to some conventional indirect bonding methods. Furthermore, the hat (34) forms a distinct, protective covering each orthodontic bracket (10). Making individual covers (34) over each bracket (10) or attachment device (13) ensures accurate placement by the tray (32). That is, the coating (34) does not encapsulate the dental restorative materials (26, 28) coated on the bracket base (22) and contact the tooth surfaces (30). The softer or more pliable inner protective coating (34) covering the bracket (10) does not interfere with the tray material (32). That is, the protective covering (34) is a discontinuous coating covering each bracket (10) separately and distinctly. This differs from conventional systems that treat the brackets (10) as a unitary structure, and use a continuous coating to cover the brackets (10).

Preferably, the polymeric coating (34) used to cover the bracket (10) comprises polyvinylsiloxane or polyether impression material, although other materials may be used. For example, RTV™ silicone (General Electric), raw silicone material such as Memosil™ (Heraeus-Kulzer), or dental wax, can be applied over the brackets (10). When the bracket (10) is covered in this manner, a protective coating (34) is formed that keeps the bracket (10) from becoming embedded in the transfer tray (32). The coating (34) further prevents undercuts or protrusions of the brackets (10) from interfering with the transfer tray (32). The coating (34) may be transparent, translucent, or colored.

Preferably a translucent, blue-tinted coating (34) is used. Such protective coatings (34) are most useful for ceramic brackets. The blue protective coating (34) can transmit blue light needed for light-curing of dental materials (26, 28). Furthermore, the blue tint is preferable because it can be seen in the mouth and easily distinguished from the clear or white ceramic brackets. More particularly, when the transfer tray (32) is removed from the patient's mouth, as described further below, some residual coating material (34) may remain in the oral cavity and this can be difficult to detect. If the coating material (34) is tinted or colored, the clinician can immediately see the material (34). The blue tint makes the protective coating (34) easier to see and thus a dental clinician can better remove any residual material left on the brackets after the transfer tray (32) is removed from the mouth. The tinted or colored coating material (34) is distinguishable to the clinician or assistants using his/her natural eyesight. If the coating is tinted, the tint should allow the penetration of blue, light, which is necessary for light-curing the dental materials (26, 28). For instance, a yellow tint would interfere with the polymerization of light-curable dental materials on the brackets. The use of a blue-tinted cover material (34) is particularly useful for translucent appliances such as ceramic brackets (10).

Next, a transfer tray (32) is made by placing a plastic sheet over the model (8) containing the attached brackets (10). The transfer tray (32) can be made using a vacuum thermoforming or pressure thermoforming machine such as, for example, the Essix® Machine, available from Dentsply Raintree or the Erkodent™ device vacuum-forming device (from Orthodent in Toronto Canada or Glidewell Labs in California) or the Drufomat™ (pressure-forming device) machine (Dentsply Raintree). Using vacuum-thermoforming, the plaster dental model (8) is placed on the vacuum plate of the machine. A sheet of thermoplastic resin is placed in the machine frame. The heating element is swung over the plastic sheet (or vice versa) and the sheet is heated until it begins to slightly sag. Then, the vacuum is turned on and the heated plastic sheet is lowered over the model (8). Alternatively, the heated plastic is lowered over the model (8) and air pressure over the sheet to form the sheet onto the model (8) using the Drufomat™ device. As the softened heated plastic begins to conform to the model (8), a probe or dental instrument may be used to guide the molten plastic into the inter-proximal undercuts of the model (8). This ensures that each tooth (30) on the model (8) is completely and tightly covered with the softened plastic. After this thermoforming step, the softened plastic is allowed to be cool to form a hardened tray (32).

In the next step, the tray (32) and attached brackets (10) are removed from the model (8). If needed, the tray (32) and model (8) (with the brackets (10) and/or other lingual buttons (13) attached thereto) can be placed in a pan of water. Soaking the tray (32) and model (8) in water helps loosen the tray (32) from the model (8). The technician may use other dental instruments such as explorers and scalars to cleanly separate the tray (32) from the model (8). Next, the technician may use scissors to trim away excess tray material (32). The tray and its appliances are removed from the model (8) and trimmed to make intraoral placement easier.

In FIGS. 3 and 4, a hardened and trimmed tray (32) is shown positioned over the dental model (8). The tray material (32) forms a close fit over the covered brackets (10) and teeth (30) on the model (8), but it does not engage any undercuts or protrusions of the brackets (10) themselves because of their protective coating (34). The coated brackets (10) do not become embedded in the tray material (32). The tray material (32) tightly conforms to the shape of the model (8) on the underside (side facing the model) and less exactly on the outer side. The close fit to the model (8) ensures that the tray (32) will be properly and securely placed on the teeth (30) when transferred to the patient. Furthermore, the tray material (32) can have high tear strength because the undercuts of the brackets (10) are not molded into the tray material (32) and tearing is not necessary to release the brackets (10). Thus, the method eliminates the need for using a second tray layer that is used in some conventional systems such as the Quest™ system (OrthoQuest, LLC, Lubbock, Tex.) and the aforementioned Cleary patents. In the present invention, one tray material (32) may be used that more accurately and closely conforms to the teeth. This enables the tray (32) to be seated more accurately.

A variety of materials can be used to make the transfer tray (32). The tray material used in the method of this invention should be both elastic and have high resistance to fracture. Preferably, the tray material comprises a blend of ethylene vinyl acetate copolymer (EVA) and siloxane. The EVA copolymer is preferably present in an amount in the range of 80 to 99% by weight. The siloxane is preferably present in an amount in the range of 0.1 to 10% by weight, and more preferably 2 to 7%.

As shown in Table 1 below, the EVA copolymer provides the tray material with more elasticity (lower elastic modulus) and elongation before fracture in contrast to other materials such as polyethylene terephthalate (PETG). The tray material made from the EVA and siloxane composition has surprisingly new and useful properties making it ideal for indirect bonding method of this invention. These properties include higher sheet strength when heated, and more uniform forming of the material (32) over the dental model (8), with less distortion of the thickness. The EVA/silicone tray material (32) further provides a lubricating surface that is less adhesive than other thermoforming materials including materials that only contain EVA. As a result, the sheet can be heated to a higher temperature than EVA is usually heated, and yet it will not bond strongly to the model (8) or the orthodontic appliances (10) or occlusal material/lingual buttons (11, 13) or the protective material (34) on the model (8). This lubricating surface also leads to easier removal of the tray (32) from the appliances (10) intra-orally. In addition, the EVA/silicone tray material (32) is more resistant to polymer "creep". EVA or copolymers of EVA are known to have less "memory" therefore, less creep (distortion) over time. As a result, the tray material has better stability over time, less polymeric creep, and substantially retains the exact shape of the model (8). As a result, the clinician can reuse the trays (32) during treatment. For instance, if a bracket (10) is dislodged by trauma during treatment, the tray (32) can be used to accurately re-position the brackets (10). The tray material provides enhanced dimensional stability.

In below Table 1, the lower elastic modulus is of the tray material (32) vs. conventional PETG material is shown. Although the tensile strengths are similar or perhaps lower for the EVA tray material (32), the much higher elongation of the EVA material before breakage or before yielding is part of the key to its success as a tray material (32). The tray material (32) has lower tear strength than conventional PETG tray material. This is counterbalanced by high elongation and high resiliency, which makes placement, positioning, and removal of the tray (32) from the mouth much easier than other trays. Furthermore, at a very low strain, the PETG material starts to deform, as indicated by the low elongation at yield for the PETG material. Of course, the inner tray material (PVS) has a much lower tensile strength compared to the other two tray materials to facilitate its removal from the undercuts of the devices (10, 13).

Furthermore, the properties of the EVA/silicone tray material (32) are such that the tray can be sectioned if needed for convenience. This may be useful when a palatal expander is removed after treatment begins, or when difficulties with access in the oral cavity are encountered, or for the aforementioned situation of replacing a bracket dislodged due to trauma.

TABLE 1

|  | PETG *Usually used as an outer tray material | EVA Tray material | PVS *Usually used as an inner tray material |
|---|---|---|---|
| Tensile elastic modulus (MPa) | 1,900 to 2,200 | 60.4 | 2.3 to 8.3 |
| Tensile strength (MPa) | 26 to 59 | 21.6 | 0.2 to 6 |
| Flexural strength (MPa) | 79 | | |
| Elmendorf tear strength (g) | 1,400 to 1,700 | 240 | |
| Elongation @ yield (%) | 4 | | |
| Elongation at Break (%) | 100 to 400 | 810 | 60 to 150 |
| Vicat softening pt @ 10 N (° C.) | 78 to 85 | 54 | |
| Heat Deflection Temp (° C.) | 64 to 70 | | |
| Melt Temp (° C.) | 260 | 84 | |
| Thermoforming temperature (° C.) | 120 to 160 | 125 to 175 | |

After removal from the model, any imperfections on the bracket base surfaces (22) can be corrected, if custom bases were made using the pre-cemented method (or if APC™ brackets are cured on the model), and the tray (32) with its embedded dental devices is stored for later use when it will be inserted in the patient's mouth. If APC™ brackets were used and the adhesives not cured, the tray (32) is carefully stored so that it is not exposed to actinic radiation before being presented for insertion in the patient. The tray (32) having the attached coated brackets (10) is stored in a protective container, such as a black bag or box, for later use. The container can be shipped to the dental office, where the clinician can precisely position and bond the brackets (10) to the patient's teeth as discussed further below.

II. Positioning the Transfer Tray in Patient's Mouth at Dental Office

The dental clinician prepares the patient's tooth surfaces (37, 39) at the dental office. The tooth surfaces (37, 39) can be polished using conventional prophylaxis pastes and other materials. Preferably an air-powder polishing technique is used to clean the surfaces where the brackets (10) or other devices (11, 13) are to be affixed. A powder slurry such as a Danville Engineering micro-etcher filled with SA-85 alumina powder can be used to polish the tooth surfaces. A prophy jet, using a Jetshield™ device to limit spray of the powder, can be used to clean and prepare the tooth surfaces. Once the tooth surface has been cleaned, it can be etched with an acid etchant such as a phosphoric acid gel. The etched surface is rinsed with water and the surface is dried. Then, the tooth surface is treated with a bonding agent such as Prime & Bond NT™ (Dentsply), and the bonding agent is light-cured for about ten (10) seconds. Preferably, two coats of bonding agent are applied to the tooth surface. In other instances, the tooth surface may be coated with a self-etching dental material that etches, primes, and bonds in a single step. For example, Xeno IV™, a one-component, light-curable, self-etching dental restorative material (Dentsply) can be used. If pre-cemented brackets are used with custom bases, a priming agent can be coated onto the bracket bases (28) in the transfer tray (32). For example, Prime & Bond NT™ bonding agent (Dentsply) can be coated over the bracket base (28) and cured. Next, a dental restorative is applied to the bracket bases (28) in the tray (32); this restorative material functions as an adhesive and is not light-cured at this time. The restorative does not need to be "buttered" into the brackets (10), like conventional orthodontic adhesives, because the brackets (10) have been prepared with custom base surfaces (22) using the pre-cemented restorative materials (26, 28) as described above. This reduces time spent preparing the brackets or other devices chair-side and drastically reduces the amount of restorative material that must be cured chair-side. This has the additional benefits that bonding strength is more quickly developed than with other indirect techniques such as using the APC™ brackets (3M) for indirect bonding or the Quest™ (OrthoQuest) techniques, where the adhesive in the entire base must be cured chair-side. This restorative material, acting as an adhesive, preferably has an intermediate viscosity so the bracket (10) can be seated without distorting the tray (32) or forming bubbles in the restorative material and thus creating a thin film over the teeth. Preferably, the restorative has a viscosity in the range of in the range of 2000 to 5000 (Pa·s). In other embodiments, the restorative can be chemically (self)-cured or dual-cured by light and chemical reaction. This restorative can be referred to as the third dental restorative material, functioning as an adhesive, herein. In one embodiment, a portion of the third restorative material is applied to the tooth surfaces, and a second portion of the material is applied to the base (22) of the brackets (10).

A thin layer of the third dental restorative acting as an adhesive is used to bond the appliances to the teeth. This thin layer helps prevents bracket distortion and ensures accurate positioning of the brackets. Some conventional indirect bonding techniques use thicker layers of ordinary bonding adhesive, making it more difficult to accurately position the brackets. If APC™ (3M) brackets are used, the indirect bonding tray should be removed from its light-protective case and immediately placed intra-orally for curing with actinic radiation.

Figure 5:
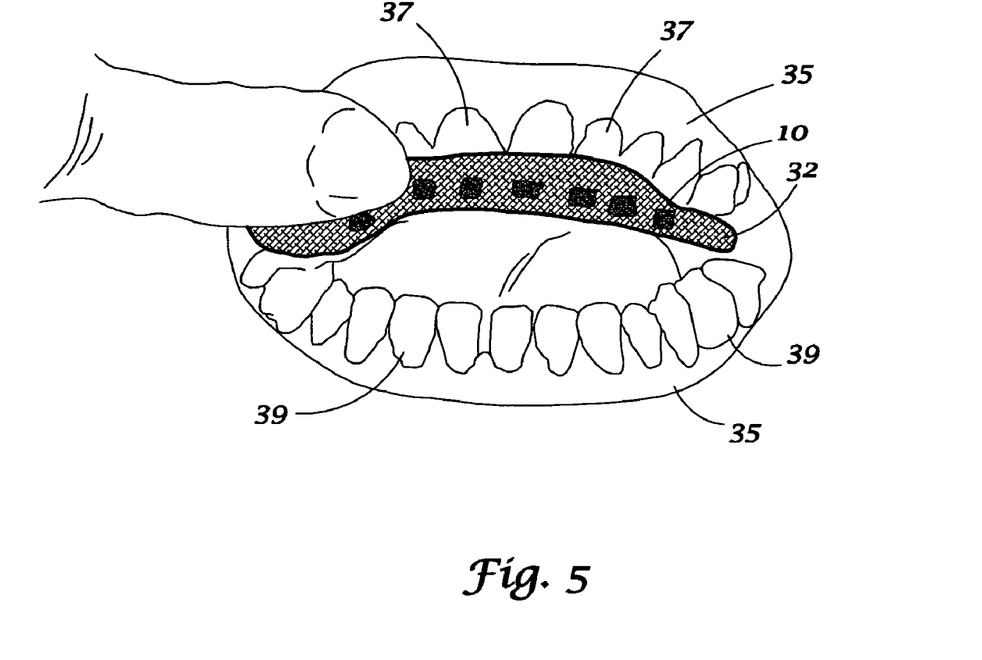
FIG. 5 is a front perspective view showing the transfer tray with releasably attached brackets being fitted in position over the upper dental arch of a patient in accordance with this invention.

Referring to FIG. 5, the tray (32) (with the attached brackets (10) is shown being placed into the patient's mouth. Using finger pressure on the occlusal or incisal portions of the teeth, the clinician places the tray (32) over the upper teeth (37). It should be understood that FIG. 5 shows the tray (32) being placed over the upper teeth (37) for illustration purposes only. In a similar manner, the tray (32) can be placed over the lower teeth (39). To hold the tray (32) in position, the clinician should press the tray using occlusal or incisal pressure only. Buccal pressure can potentially cause the brackets (10) to rotate, slide or change position. Occlusal or incisal pressure produces a more consistent accurate bracket-bonding placement. No pressure is required on the facial or lingual portions of the tray (32) because of the tray's close approximation to the tooth surfaces (37) and its high elasticity and lack of an inner layer of material. The tray material (32) used in this invention is designed to be stiffer than conventional inner tray layers. Furthermore, because of the protective coatings (34) over the brackets (10), more flexibility of the transfer tray (32) is possible and desirable. This allows for safe removal of the tray (32) without dislodging the brackets (10). Because of the design of the transfer tray (32) and dental materials (26, 28), the tray of this invention has a closer approximation to each tooth (37) than conventional transfer trays. The tray (32) used in the method of this invention is a unitary tray. That is, the tray (32) is single-piece structure made of one layer of material—it does not consist of an inner and outer tray material. Without an inner tray, the clinician can position a light-curing gun closer to the bracket base surface (22) at the mesial, distal, gingival and occlusal or incisal edges of the brackets (10) and there is less tray material (32) to penetrate. The tray (32) conforms to the dental arches (37, 39) more closely, and the brackets (10) can be positioned more accurately.

Figure 6:
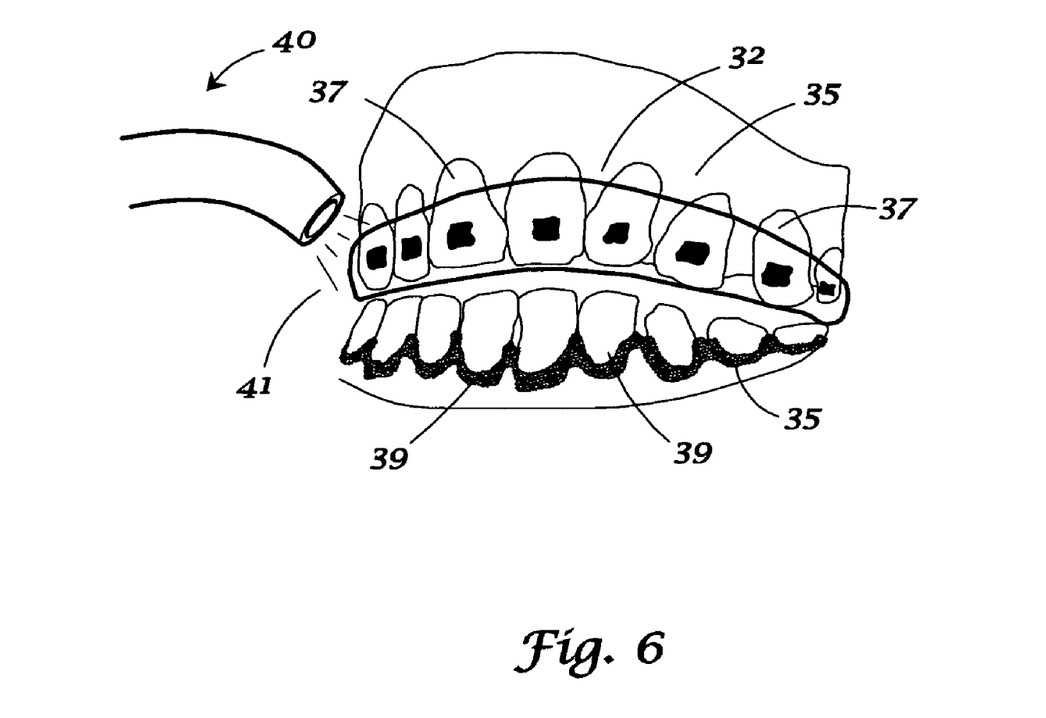
FIG. 6 is a front perspective view showing the brackets releasably attached to the transfer tray being bonded to the upper tooth surfaces of a patient in accordance with this invention.

As shown in FIG. 6, once the transfer tray (32) has been properly positioned, the clinician uses a dental curing light (40) to direct light radiation (41) against each bracket (10) to bond them to the respective tooth (37). Using this light-curing method, the brackets (10) are firmly bonded to the teeth (37). The tray (32) is then removed from the mouth, while the brackets (10) remain tightly bonded to the teeth (37). Any residual coating material, which formed the protective coating (34) over the brackets (10), is removed at this point. Now the arch wire (not shown) is ready to be inserted into the slots of the brackets (10). The force of the archwire and brackets (10) will move the teeth (37) to their desired location.

The indirect bonding method of this invention provides many benefits. For example, rapid bonding of the brackets to posterior teeth in the mouth (as far back as the third molars) can be achieved. Bonding brackets to second or third molars is very difficult using direct bonding techniques. In fact, bonding brackets to these posterior teeth, such as the second or third molars, is not usually performed because of the difficulty in achieving a "dry field" in the posterior region of the mouth. Physically, the orthodontist is impeded from accurately placing the brackets on such teeth, because of the close proximity of the cheek and the curve of the dental arch at the posterior area of the mouth. A dental mirror is difficult to insert in such locations, much less an instrument with a bracket that needs to be accurately cured in position. The mal-positioning of the second molars can potentially contribute to temporal mandibular joint disease and occlusal instability. However, with the indirect bonding method of this invention, no obstructions to placement occur from the tissue, tongue, or throat. Special instruments are not required to place brackets on the second or third molars, and impeded vision is not a problem with the indirect bonding technique. Using this new method, the problems with correcting the position of the second or third molars can be addressed.

Another benefit of the indirect bonding technique is that it helps prevent the ingestion or aspiration of orthodontic appliances. Orthodontic appliances have become smaller with new designs and are more difficult to hold. The appliances are secured in the tray when inserted intra-orally, and they are unlikely to be dislodged during placement or curing of the restorative (adhesive) material. This eliminates the scenario of a bracket becoming loose during placement and curing procedures, as can occur in direct bonding procedures.

Workers skilled in the art will appreciate that various modifications can be made to the illustrated embodiments and description herein without departing from the spirit and scope of the present invention. It is intended that all such modifications within the spirit and scope of the present invention be covered by the appended claims.

The invention claimed is:

1. A method of indirectly bonding a plurality of orthodontic appliances to a plurality of teeth, each of the plurality of teeth having a tooth surface, comprising the steps of:
   a. providing a plurality of orthodontic appliances having a main body with a tooth-engaging surface;
   b. making a dental model of a patient's tooth anatomy, the dental model having a plurality of teeth;
   c. positioning the plurality of orthodontic appliances on the model;
   d. applying a polymeric material to cover at least a portion of the main body of each of the orthodontic appliances so that each of the plurality of orthodontic appliances does not interfere with a tray that is subsequently formed over the model and wherein the polymeric material does not contact the plurality of teeth of the model;
   e. forming the tray over the model so the tray conforms to the shape of the model and the plurality of orthodontic appliances become releasably attached to the tray;
   f. removing the tray with the attached plurality of orthodontic appliances from the model;
   g. preparing the tooth surfaces of a patient to be fitted with the plurality of orthodontic appliances;
   h. pressing the tray into position in the mouth of the patient so the plurality of orthodontic appliances are positioned and bonded to the tooth surfaces; and
   i. removing the tray from the mouth while the plurality of orthodontic appliances remain bonded to the tooth surfaces.

2. The method of claim 1, wherein a separating liquid is applied to the model prior to positioning at least one of the plurality of orthodontic appliances on the model.

3. The method of claim 1, wherein the tooth engaging surface of the plurality of orthodontic appliances is coated with at least one dental restorative material.

4. The method of claim 3, wherein the at least one dental restorative material comprises a first dental material having a viscosity in the range of 1.4 to 1000 Pascal-seconds (Pa·s) and a second dental material having a viscosity in the range of 2000 to 5000 Pascal-seconds (Pa·s), the first dental material being cured and the second dental material being uncured prior to positioning the plurality of orthodontic appliances on the model.

5. The method of claim 4, further comprising the step of curing the second dental material after positioning the plurality of orthodontic appliances on the model.

6. The method of claim 3, wherein the at least one dental restorative material comprises a dental material having a viscosity in the range of 1.4 to 5000 Pascal-seconds (Pa·s), the method further comprising the step of curing the dental material on the model.

7. The method of claim 6, further comprising the step of curing the at least one dental restorative material after positioning the plurality of orthodontic appliances on the model.

8. The method of claim 3, wherein the at least one dental restorative material is uncured and the coated plurality of orthodontic appliances are stored in a light-curable protective container for later use.

9. The method of claim 3, wherein the at least one dental restorative material comprises an adhesive, the adhesive being uncured prior to positioning the plurality of orthodontic appliances on the model.

10. The method of claim 9 further comprising the step of light-curing the adhesive after positioning the plurality of orthodontic appliances on the model.

11. The method of claim 1, wherein the polymeric material used to cover at least a portion of the plurality of orthodontic appliances comprises polyvinylsiloxane.

12. The method of claim 1, wherein the polymeric material used to cover at least a portion of the plurality of orthodontic appliances is transparent.

13. The method of claim 1, wherein the polymeric material used to cover at least a portion of the plurality of orthodontic appliances is translucent.

14. The method of claim 13, wherein the translucent polymeric material is blue-tinted.

15. The method of claim 1, wherein the polymeric material used to cover at least a portion of the plurality of orthodontic appliances is colored.

16. The method of claim 1, wherein the tray comprises a thermoplastic resin.

17. The method of claim 16, wherein the thermoplastic resin comprises a blend of ethylene vinyl acetate copolymer and siloxane.

18. The method of claim 1, wherein the step of preparing the tooth surfaces of the patient comprises polishing the tooth surfaces of the patient with a dental polishing agent or dental prophylaxis agent.

19. The method of claim 1, wherein the step of preparing the tooth surfaces of the patient comprises first acid-etching the tooth surfaces of the patient with an acid etchant and then treating the tooth surfaces of the patient with a bonding agent.

20. The method of claim 1, wherein the step of preparing the tooth surfaces of the patient comprises treating the tooth surfaces of the patient with a self-etching primer material.

21. The method of claim 1, wherein prior to the step of pressing the tray into position in the mouth of the patient, the plurality of orthodontic appliances are coated with a first dental material after the tray with the attached plurality of orthodontic appliances has been removed from the model.

22. The method of claim 21, further comprising the step of chemically or dual-curing the first dental material after the plurality of orthodontic appliances are positioned on the tooth surfaces of the patient.

23. The method of claim 22, wherein the at least one dental restorative material has a viscosity in the range of 2000 to 5000 Pascal-seconds (Pa·s).

24. The method of claim 22, wherein the tray comprises a blend of ethylene vinyl acetate copolymer and siloxane.

25. The method of claim 21, the first dental material being uncured prior to pressing the tray into position in the mouth of the patient.

26. The method of claim 1, wherein prior to the step of pressing the tray into position in the mouth of the patient, the plurality of orthodontic appliances are coated with a first dental material having a viscosity in the range of 1.4 to 1000 Pascal-seconds (Pa·s) and the tooth surfaces of the patient which will receive the plurality of orthodontic appliances are coated with a second dental material having a viscosity in the range of 2000 to 5000 Pascal-seconds (Pa·s).

27. The method of claim 26, further comprising the step of light-curing the first dental material prior to positioning the plurality of orthodontic appliances on the second dental material that is coated on the tooth surfaces of the patient.

28. The method of claim 1, wherein the polymeric material is applied in a discontinuous manner so that each of the plurality of orthodontic appliances are separately and distinctly covered.

29. A method of indirectly bonding a plurality of orthodontic appliances to a plurality of teeth, each of the plurality of teeth having a tooth surface, comprising the steps of:
  a. providing a plurality of orthodontic appliances having a main body with a tooth-engaging surface, the tooth-engaging surfaces being coated with a first dental material having a viscosity in the range of 1.4 to 1000 Pascal-seconds (Pa·s);
  b. curing the first dental material after being applied to the tooth engaging surfaces;
  c. making a dental model of a patient's tooth anatomy, the dental model having a plurality of teeth;
  d. applying a second dental material having a viscosity in the range of 2000 to 5000 Pascal-seconds (Pa·s) to the cured surfaces of the first dental material;
  e. positioning the plurality of orthodontic appliances on the model;
  f. curing the second dental material after positioning the plurality of orthodontic appliances on the model;
  g. applying a polymeric material to cover at least a portion of the main body of each of the plurality of orthodontic appliances so that each of the plurality orthodontic appliances do not interfere with a tray that is subsequently formed over the model, the polymeric material is applied in a discontinuous manner so that each of the plurality of orthodontic appliances are separately and distinctly covered and wherein the polymeric material does not contact the plurality of teeth of the model;
  h. forming the tray over the model so the tray conforms to the shape of the model and the plurality of orthodontic appliances become releasably attached to the tray;
  i. removing the tray with the attached plurality of orthodontic appliances from the model;
  j. preparing the tooth surfaces of a patient to be fitted with the plurality of orthodontic appliances;
  k. applying at least one dental restorative material to the coated tooth-engaging surfaces of the plurality of orthodontic appliances and pressing the tray into position in the mouth of the patient so the plurality of orthodontic appliances are positioned and bonded to the tooth surfaces of the patient; and
  l. removing the tray from the mouth while the plurality of orthodontic appliances remain bonded to the tooth surfaces.

* * * * *